United States Patent [19]

D'Silva

[11] 4,058,549
[45] Nov. 15, 1977

[54] N-SUBSTITUTED CYANOALKANE-SULFENYL (AND THIOSULFENYL)-N-ALKYL CARBAMOYL HALIDES

[75] Inventor: Themistocles D. J. D'Silva, South Charleston, W. Va.

[73] Assignee: Union Carbide Corporation, New York, N.Y.

[21] Appl. No.: 701,166

[22] Filed: June 30, 1976

[51] Int. Cl.² ................ C07C 121/417; C07C 121/46
[52] U.S. Cl. ................................ 260/465.4; 260/464; 260/544 C
[58] Field of Search .............................. 260/465.4, 464

[56] References Cited

U.S. PATENT DOCUMENTS

| 3,639,471 | 2/1972 | Klauke et al. | 260/544 C |
| 3,699,163 | 10/1972 | Kohn | 260/544 C |
| 3,843,689 | 10/1974 | Brown | 424/300 X |
| 3,847,951 | 11/1974 | Kohn et al. | 424/285 X |
| 3,890,386 | 6/1975 | Kuhle et al. | 260/465.4 X |

FOREIGN PATENT DOCUMENTS

| 796,646 | 3/1973 | Belgium | |
| 2,362,686 | 6/1974 | Germany | 260/544 C |

Primary Examiner—Joseph Paul Brust
Attorney, Agent, or Firm—Richard C. Stewart

[57] ABSTRACT

N-Substituted alkanesulfenyl-N-alkyl and N-substituted alkanethiosulfenyl-N-alkyl carbamoyl halide compounds are useful as intermediates in the preparation of pesticidal carbamate compounds.

11 Claims, No Drawings

N-SUBSTITUTED CYANOALKANE-SULFENYL (AND THIOSULFENYL)-N-ALKYL CARBAMOYL HALIDES

This invention relates to a novel class of N-substituted alkanesulfenyl-N-alkyl and N-substituted alkanethiosulfenyl-N-alkyl carbamoyl halide compounds and to their preparation.

More particularly, this invention relates to compounds of the formula:

$$X-\overset{O}{\underset{\|}{C}}-\overset{R}{\underset{|}{N}}-(S)_n-\overset{R_1}{\underset{\underset{R_2}{|}}{C}}-R_3$$

wherein:

$n$ is 1 or 2;
X is chloride or fluorine;
R is alkyl;
$R_1$ and $R_2$ are individually alkyl, haloalkyl or $R_1$ and $R_2$ together may form an alkylene chain completing either a substituted or unsubstituted cyclopentyl, cylohexyl or a 6, 7 or 8 membered bicycloalkyl ring wherein the permissible substituents are one or more chloro, fluoro, bromo, alkyl or haloalkyl substituents;
$R_3$ is cyano or haloalkyl.

R, $R_1$, $R^2$ and $R_3$ substituents individually may not include more than eight aliphatic carbon atoms. Preferred because of their usefulness as intermediates in the preparation of carbamate compounds that exhibit outstanding pesticidal activity are the compounds of this invention in which:

R is methyl;
$R_1$ and $R_2$ are individually alkyl or chloroalkyl;
$R_3$ is cyano or chloroalkyl;
with the proviso that the total number of aliphatic carbons included in $R_1$, $R_2$ and $R_3$ individually does not exceed four. Particularly preferred compounds of this invention are those wherein R is methyl, $R_1$ and $R_2$ are individually methyl or chloromethyl and $R_3$ is cyano or chloromethyl.

Carbamoyl halide compounds of this invention are useful intermediates in the preparation of nematocidially, insecticidally and miticidally active carbamate compounds. The compounds of this invention can be reacted with oximes and hydroxylated aryl compounds in the presence of an acid acceptor to produce the corresponding pesticidally active carbamate compound. For example, 2-methylthio-2-methylpropionaldoxime can be reacted with N-methyl-N-(2-chloromethyl-2-propanesulfenyl)carbamoyl chloride in the presence of triethylamine as an acid acceptor to produce 2-methylthio-2-methylpropionaldehyde O-[N-methyl-N-(2-chloromethyl-2-propanesulfenyl)carbamoyl]oxime, the corresponding pesticidally active carbamate compound. The above disclosed reaction is described in more detail in my copending United States Patent Application Ser. No. 701,165 entitled N-SUBSTITUTED ALKANESULFENYL)-N-ALKYL AND N-(SUBSTITUTED ALKANETHIOSULFENYL)-N-ALKYL CARBAMATE COMPOUNDS filed concurrently herewith.

The compounds of this invention can be prepared by variety of methods. Four preferred methods are illustrated by the reaction schemes set forth below in which $n$, X, R, $R_1$, $R_2$ and $R_3$ are as described above, except as noted.

METHOD I $$X-\overset{O}{\underset{\|}{C}}-\overset{R}{\underset{|}{N}}-SCl + H-\overset{R_1}{\underset{\underset{R_2}{|}}{C}}-CN \longrightarrow X-\overset{O}{\underset{\|}{C}}-\overset{R}{\underset{|}{N}}-S-\overset{R_1}{\underset{\underset{R_2}{|}}{C}}-CN$$

METHOD II $$X-\overset{O}{\underset{\|}{C}}-\overset{R}{\underset{|}{N}}-SCl + \overset{R_1}{\underset{R_2}{\diagdown}}C=C\overset{R'}{\underset{R''}{\diagup}} \longrightarrow X-\overset{O}{\underset{\|}{C}}-\overset{R}{\underset{|}{N}}-S-\overset{R_1}{\underset{\underset{R_2}{|}}{C}}-\overset{R'}{\underset{\underset{R''}{|}}{C}}-Cl.$$

R' and R'' in METHOD II are individually hydrogen, alkyl, halogen or haloalkyl.

METHOD III $$Cl-\overset{O}{\underset{\|}{C}}-\overset{R}{\underset{|}{N}}-SCl + HS-\overset{R_1}{\underset{\underset{R_2}{|}}{C}}-R_3 \longrightarrow Cl-\overset{O}{\underset{\|}{C}}-\overset{R}{\underset{|}{N}}-S-S-\overset{R_1}{\underset{\underset{R_2}{|}}{C}}-R_3$$

METHOD IV $$F-\overset{O}{\underset{\|}{C}}-\overset{R}{\underset{|}{N}}-H + Cl-(S)_n-\overset{R_1}{\underset{\underset{R_2}{|}}{C}}-R_3 \longrightarrow F-\overset{O}{\underset{\|}{C}}-\overset{R}{\underset{|}{N}}-(S)_n-\overset{R_1}{\underset{\underset{R_2}{|}}{C}}-R_3$$

In the reactions illustrated in Methods I, II, III and IV equimolar amounts of the reactants are brought together in an inert solvent. Any inert solvent such as benzene, toluene, xylene, dioxane, tetrahydrofuran or the like can be used.

Reaction temperatures are not critical and can be varied over a wide temperature range depending to a large extent on the reactivity and the thermal stability of the reactants. Preferred reaction temperatures are from about $-30°$ C to about $100°$ C.

Reaction pressures are not critical. For convenience the reaction is usually conducted at atmospheric or autogenous pressure.

The reaction illustrated in Method IV is conducted in the presence of an acid acceptor. The acid acceptor employed is a basic material that can be either an organic or an inorganic base. The molar ratio of acid acceptor to either reactant is equimolar or a slight excess of acid acceptor may be used. Illustrative of organic bases which are useful as acid acceptors are teriary amines, alkalimetal alkoxides or the like. Bases such as potassium hydroxide, sodium hydroxide or the like are illustrative of inorganic bases that can be used as acid acceptors in the conduct of this reaction. Preferred acid acceptors are tertiary amines such as pyridine, triethylamine, 1,4-diazabicyclo [2.2.2] octane or the like.

N-Alkyl carbamoyl fluoride precursors can be prepared by reacting hydrogen fluoride with an appropriately substituted isocyanate. This procedure is described in more detail in U.S. Pat. No. 3,639,471.

N-Alkyl-N-(chlorothio)carbamoyl chloride precursors can be prepared by reacting sulfur dichloride with an appropriately substituted isocyanate as described in U.S. Pat. No. 3,699,167. N-Alkyl-N-(chlorothio)carbamoyl fluoride precursors can be prepared through the direct chlorination of the corresponding bis-(N-alkyl-N-fluorocarbonylamine) disulfide as described in detail in German Pat. Nos. 1,931,054 and 2,023,079.

The following specific examples are presented to more particularly illustrate the invention:

EXAMPLE I

Preparation of N-Methyl-N-(2-chloromethyl-2-propanesulfenyl)carbamoyl chloride.

To a solution of 22.1g of isobutylene in 150 ml of benzene was added dropwise and with external cooling (5°–10° C), 48.0g of N-methyl-N-chlorosulfenyl carbamoyl chloride dissolved in 150 ml of benzene. The reaction mixture was then stirred for an additional 1 hour at ambient temperature. Evaporation of the solvent gave 62.7g of a (1:1) isomeric mixture of product. The Markovnikov addition product decomposes on heating to yield isobutylene sulfide and other unidentified byproducts. The desired N-methyl-N-(2-chloromethyl-2-propanesulfenyl)carbamoyl chloride was isolated by distillation.
b.p. 87°–90° C/0.4mm.
Infra-red (neat) 5.82 (C=O), 8.0, 8.65, 9.8, 11.8, 12.5, 13.3 and 14.0μ.
NMR(CDCl$_3$)δ 1.40 (s), 6H; 3.49 (s), 3H; 3.78 (s), 2H.

EXAMPLE II

Preparation of N-Methyl-N-(2-methyl-1,3-dichloro-2-propanesulfenyl)carbamoyl chloride.

To a solution of 16.0g of N-methyl-N-chlorosulfenyl carbamoyl chloride in 100 ml of methylene chloride was added 12.0g of methallyl chloride with stirring, at room temperature. On slight heating there was a spontaneous exotherm which raised the temperature of the reaction mixture to 39° C. On removal of the solvent under reduced pressure 19.6g of oil was obtained. n$_D^{25}$ 1.5379.
Infra-red (neat) 5.76 (C=O), 8.0, 8.65, 9.8, 11.8, 12.25, 13.45, and 14.0μ.
NMR(CDCl$_3$)δ 1.41 (s), 3H; 3.48 (s), 3H; 3.87 (d). J$_{AB}$ =12.0 H$_Z$ and 3.97 (d), J$_{BA}$ = 12.0 H$_Z$ 4H.
Cal'd. for C$_6$H$_{10}$Cl$_3$NOS: C, 28.76; H, 4.02; N, 5.59; Found: C, 28.87; H, 3.87; N, 4.72.

EXAMPLE III

Preparation of N-Methyl-N-(1-chloro-2-cyano-2-propanesulfenyl)carbamoyl fluoride.

To a mixture of 3.53g of anhydrous hydrogen fluoride in 150 ml of toluene cooled to −50° C. was added dropwise 10.05g of methyl isocyanate. After stirring for 1.5 hr. at 0° C, 30.0g of approximately 85 percent pure 1-chloro-2-cyano-2-propanesulfenyl chloride was added followed by dropwise addition of 17.8g of triethylamine. During the addition of base the temperature was maintained between 0° C and 10° C. After stirring for an additional 1 hr., the precipitated salt was removed by filtration and the filtrate was concentrated to yield 26.5g of a light yellow oil.
Infra-red (neat) 4.53 (C|N), 5.6 (C=O), 6.4, 6.9, 7.05, 7.3, 7.7, 8.5, 9.2, 10.4, 12.4, 13.3μ.
NMR (CDCl$_3$)δ 1.65 (s), 3H; 3.50 (s), 3H; 3.73 (d), J$_{AB}$ = 12.0 H$_Z$ and 3.98 (d), J$_{AB}$ = 12.0 H$_Z$, 2H.

EXAMPLE IV

Preparation of N-Methyl-N-(2-methyl-1,3-dichloro-2-propanesulfenyl)carbamoyl fluoride.

To a solution of 1.35g of methallyl chloride in 25 ml of methylene chloride was added 2.15g of N-methyl-N-chlorosulfenyl carbamoyl fluoride. The solution was heated to reflux for 45 min. and concentrated to 1.68g of pale yellow oil.
Infra-red (neat) 5.57 (C=O), 6.9, 7.0, 7.26, 7.65, 8.45, 9.15, 10.42, 12.3, 13.3 and 14.1μ.
NMR (CDCl$_3$)δ 1.39 (s), 3H; 3.36 (d), J = 1.0 H$_Z$, 3H, 3,92 (s), 4H.

EXAMPLE V

Preparation of N-Methyl-N-(2-cyano-2-propanesulfenyl)carbamoyl chloride

Anhydrous hydrochloric acid gas was bubbled for 20 minutes through a mixture of 16.0g of N-methyl-N-chlorosulfenyl carbamoyl chloride and 7.59g of isobutyronitrile. After stirring for 26 hours the reaction mixture was distilled to yield 12.4g of yellow oil. b.p. 50° C/8 mm. N$_D^{24}$ 1.4656.
Infra-red (neat) 4.43 (C|N), 5.72 (C=O), 6.5, 6.85, 8.1, 8.6, 9.75 and 11.8.
NMR (CDCl$_3$) 1.68 (s), 6H; 3.6 (s), 3H.

EXAMPLE VI

Preparation of N-Methyl-N-(2-cyano-2-propanesulfenyl)carbamoyl fluoride

Anhydrous hydrogen chloride was bubbled through a stirred mixture of 37.65g of N-methyl-N-chlorosulfenyl carbamoyl fluoride and 19.82g of isobutyronitrile for 30 minutes at room temperature. After stirring for 72 hours the reaction mixture was distilled to yield 41.4g of yellow oil b.p 50° CC/5 mm. N$_D^{24}$ 1.5011.
Infra-red (neat) 4.41 (C|N), 5.52 (C=O), 6.4, 6.8, 7.6, 8.1, 9.1, 9.25, 10.35 and 13.25.
NMR (CDCl$_3$) 1.65 (s), 6H; 3.51 (d), J=1.0 H$_Z$, 3H.
Calc'd. for C$_6$H$_9$FN$_2$OS: C, 40.89; H. 5.15; N, 15.90
Found: C, 40.19; H, 5.06; N, 15.47.

EXAMPLE VII

Preparation of N-Methyl-N-(2-cyano-2-propanethiosulfenyl)carbamoyl fluoride.

To a mixture of 36.66g of anhydrous hydrogen fluoride in 300 ml of toluene cooled to −50° C was added dropwise and with stirring, 104.3 ml of methyl isocyanate over a period of 40 minutes. After stirring for 1 hour at 0° C, 306.94g of 2-cyano-2-chlorothiosulfenylpropane dissolved in 500 ml of toluene was added followed by a slow addition of 185.0g of triethylamine, whilst maintaining the temperature between 3° and 10° C. After stirring for a period of 3 hours, the reaction was quenched with water and the toluene solution was dried over magnesium solfate. Removal of the solvent yielded 206.9g of an oil which solidified on standing. Crystallization from hexane-isopropylether gave a solid with m.p. 42°–45° C.
Calc'd for C$_6$H$_9$FN$_2$OS$_2$: C, 34.60; H, 4.35; N, 13.45.
Found: C, 34.55; H, 4.20; N, 13.33.

The following compounds are representative of other compounds that are within the scope of this invention which can be prepared according to this invention by selecting appropriate starting materials for use in the procedure above.

N-Methyl-N-(1-chloro-2-methyl-2-pentanesulfenyl)-carbamoyl chloride.

N-Methyl-N-(1,3-dichloro-2-methyl-2-propanethiosulfenyl)carbamoyl fluoride.

N-Methyl-N-(1-chloromethyl-1-cyclohexanesulfenyl)carbamoyl chloride.

N-Methyl-N-(2-chloro-1-methyl-1-cyclopentanesulfenyl)carbamoyl fluoride.

N-Methyl-N-(3-chloro-2-methyl-2-butanesulfenyl)-carbamoyl chloride.

N-Methyl-N-(1-chloro-2,3,3-trimethyl-2-butanesulfenyl)carbamoyl chloride.

N-Methyl-N-(1-chloro-2-cyano-2-propanethiosulfenyl)carbamoyl fluoride.

N-Methyl-N-(3-chloro-2,3-dimethyl-2-pentanesulfenyl)carbamoyl fluoride.

N-Methyl-N-(3-cyano-3-pentanethiosulfenyl)carbamoyl fluoride.

N-Hexyl-N-(3-bromo-2-methyl-2-butanethiosulfenyl)carbamoyl chloride

N-Isopropyl-N-(2-cyano-2-bicyclo[2.2.1]heptanethiosulfenyl)carbamoyl chloride

What is claimed is:

1. A compound of the formula:

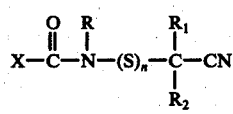

wherein:
$n$ is 1 or 2;
$X$ is chlorine or fluorine;
$R$ is alkyl;
$R_1$ and $R_2$ are individually alkyl or haloalkyl or $R_1$ and $R_2$ together may form an alkylene chain completing either a substituted or unsubstituted cyclopentyl, cyclohexyl or either a 6, 7 or 8 membered bicycloalkyl ring wherein the permissible substituents are one or more chloro, fluoro, bromo, alkyl or haloalkyl substituents;
with the proviso that $R$, $R_1$, and $R_2$ substituents individually may not include more than eight aliphatic carbon atoms.

2. A compound according to claim 1 wherein $R_1$ and $R_2$ are individually alkyl or chloroalkyl substituted with from 1 to 5 chlorine atoms.

3. A compound according to claim 1 wherein $R_1$ and $R_2$ are individually methyl or chloromethyl.

4. A compound according to claim 1 wherein $n$ is 1.

5. A compound according to claim 1 wherein $n$ is 2.

6. A compound according to claim 1 wherein $X$ is fluorine.

7. A compound according to claim 1 wherein $X$ is chlorine.

8. N-Methyl-N-(2-cyano-2-propanesulfenyl)carbamoyl fluoride.

9. N-Methyl-N-(2-cyano-2-propanethiosulfenyl)carbamoyl fluoride.

10. N-Methyl-N-(2-cyano-2-propanesulfenyl)carbamoyl chloride.

11. A method of preparing a compound of the formula:

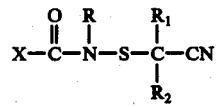

which comprises reacting a compound of the formula:

and a compound of the formula:

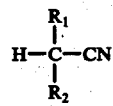

wherein:
X is chlorine or fluorine;
R is alkyl;
$R_1$ and $R_2$ are individually alkyl or haloalkyl or $R_1$ and $R_2$ together may form an alkylene chain completing either a substituted or unsubstituted cyclopentyl, cyclohexyl or either a 6, 7 or 8 membered bicycloalkyl ring wherein the permissible substituents are one or more chloro, fluoro, bromo, alkyl or haloalkyl substituents. with the proviso that R, $R_1$ and $R_2$ substituents individually may not include more than eight aliphatic carbon atoms.

* * * * *